United States Patent [19]

Bell

[11] Patent Number: 5,060,636

[45] Date of Patent: Oct. 29, 1991

[54] CHIROPRACTIC TABLE

[76] Inventor: William M. Bell, 1743 Highway 88 West, Brick Town, N.J. 08723

[21] Appl. No.: 299,303

[22] Filed: Jan. 23, 1989

[51] Int. Cl.[5] .................. A61F 5/00

[52] U.S. Cl. .................. 128/72; 5/66; 5/68; 128/75; 269/328

[58] Field of Search .................. 128/68, 69, 72, 75, 128/70, 71; 5/435, 66-69; 269/328

[56] References Cited

U.S. PATENT DOCUMENTS

| | | | |
|---|---|---|---|
| 1,950,948 | 3/1934 | Murray | 128/72 |
| 3,226,106 | 12/1965 | Johnson et al. | 128/72 X |
| 4,655,200 | 4/1987 | Knight | 128/75 X |
| 4,672,952 | 6/1987 | Vrzalik | 128/75 X |
| 4,757,983 | 7/1988 | Ray et al. | 125/435 X |

FOREIGN PATENT DOCUMENTS

| | | | |
|---|---|---|---|
| 1181663 | 9/1985 | U.S.S.R. | 128/75 |

*Primary Examiner*—Edgar S. Burr
*Assistant Examiner*—Moshe I. Cohen
*Attorney, Agent, or Firm*—Clifford G. Frayne

[57] ABSTRACT

An improved chiropractic table for spinal adjustment of lateral curvature of the spine wherein a segmented chiropractic table has positioned on its longitudinal sides, a plurality of lateral compressor adjustment arms longitudinally disposed along the side of the table and laterally adjustable inwardly to contact or engage the mid torso of the patient to permit the doctor to provide selective, repeated lateral compression on the spine of the patient.

6 Claims, 2 Drawing Sheets

CHIROPRACTIC TABLE

FIELD OF INVENTION

This invention relates to an improved chiropractic table for use by chiropractors and osteopaths in performing the skeletal adjustments on the patient and, in particular, applies to an improved chiropractic table which permits the chiropractor to position the body of the patient and provide repeated, measured, skeletal adjustments to the patient.

BACKGROUND OF THE INVENTION

Chiropractic tables consist of segmented tables with each segment being cushioned to support the particular portion of the patient's anatomy. The tables are designed to permit the doctor to place attention on the spinal column in order to relieve pressure and to perform a variety of other skeletal adjustments. Many improvements to chiropractic tables have been made over the years as evidenced by the following patents: U.S. Pat. No. 2,023,429; U.S. Pat. No. 4,354,485; U.S. Pat. No. 1,950,948; U.S. Pat. No. 1,126,460; U.S. Pat. No. 1,234,536; U.S. Pat. No. 1,374,115; U.S. Pat. No. 1,536,354; U.S. Pat. No. 1,582,950; U.S. Pat. No. 2,002,349; U.S. Pat. No. 4,271,830; and U.S. Pat. No. 4,579,109.

Applicant's invention comprises a segmented chiropractic table with chin rest; however, Applicant's table permits the doctor to provide measured lateral pressure upon the patient and thus the spinal column through the use of track mounted lateral pressure arms slidably mounted on a track and adjustable by means of a crank and worm gear to permit the doctor to provide adjustable, measured lateral pressure to the patient and the patient's spine.

SUMMARY OF THE INVENTION

The present invention utilizes a segmented padded chiropractic table having a first longitudinal end which provides a chin rest for the patient, a second longitudinal end which provides for foot stirrups for the patient and a means for adjusting the longitudinal tension on the patient's spine. Mounted along the longitudinal edges of the chiropractic table are a series of track mechanisms allowing for the slidable adjustment of padded lateral compressor arms slidable in the track mechanism for adjustment for the portion of the body to which they will be compressed, each of the pressure arms operable by means of a crank and worm gear, so as to move the compressor arms laterally inwardly to contact the patient's body, each of the track mechanisms also operable by means of a crank and worm gear to move the entire track mechanism laterally inwardly such that the compressor arms contact the patient's anatomy.

OBJECTS OF THE INVENTION

The object of the present invention is to provide a novel and improved chiropractic table.

A further object of the present invention is to provide a chiropractic table with improved thoracic support for adjusting tension on the patient's spine.

A further object of the present invention is to provide for measured lateral adjustment of the spine.

A still further object of the present invention is to provide for a novel and improved chiropractic table which permits the repeated, measured lateral adjustment to the spine.

A still further object of the present invention is to provide for a novel and improved chiropractic table which permits the repeated, measured lateral adjustment to the spine at a plurality of longitudinal locations and at various degrees of compression.

BRIEF DESCRIPTION OF THE DRAWINGS

A better understanding of the present invention as well as other objects and advantages thereof will become apparent upon consideration of the detailed disclosure thereof especially when taken with the accompanying drawings wherein.

DETAILED DESCRIPTION OF THE DRAWINGS

Figure 1:
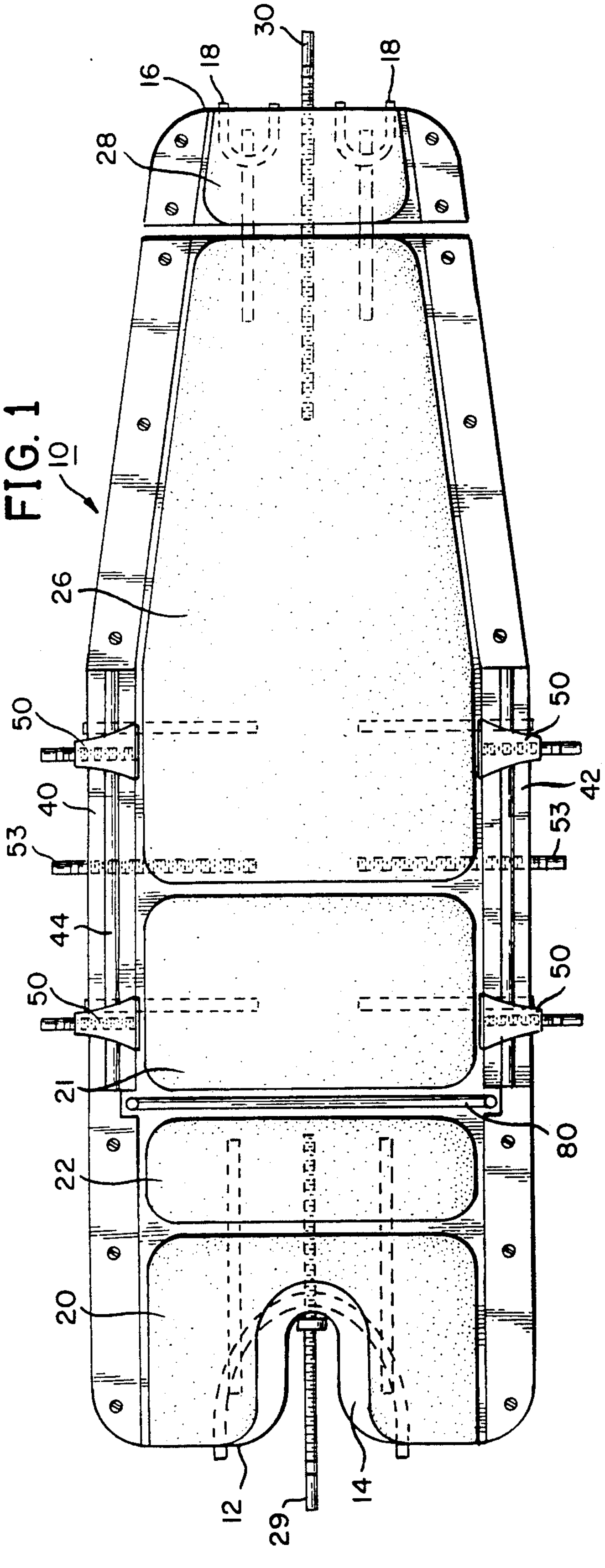
FIG. 1 is a top planer view of the improved chiropractic table.
Figure 2:
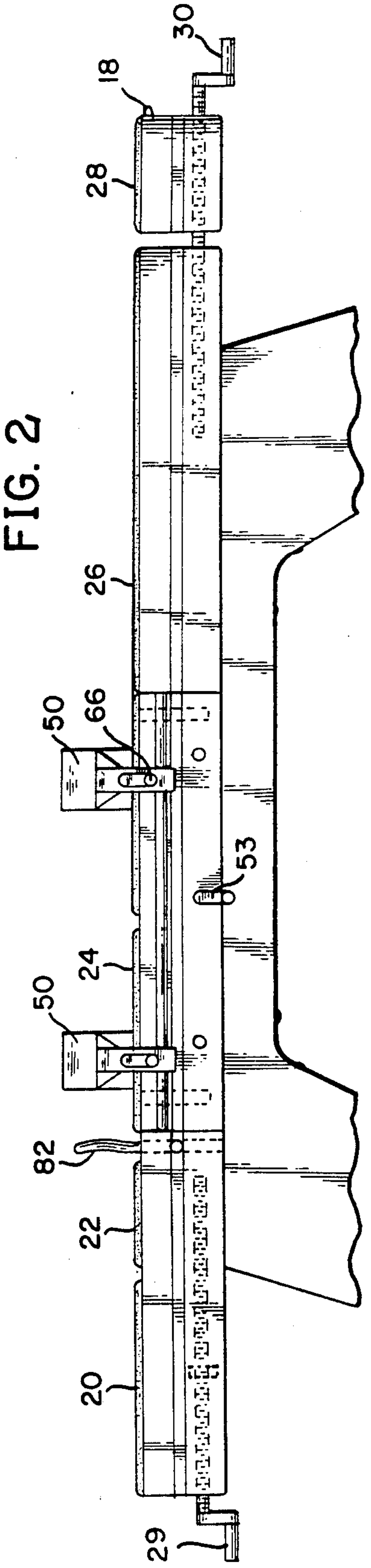
FIG. 2 is a side elevational view of the improved chiropractic table.

Referring to FIG. 1 and 2, there is shown a top planer view of the improved chiropractic table 10 and a side view. Chiropractic table 10 has a first longitudinal end 12 defining a neck, chin or thoracic rest 14 and a second longitudinal end 16 defining a foot brace or foot stirrup mount 18. The chiropractic table 10 is constructed in segmented form, and in this embodiment, contains five padded segmented portions 20, 22, 24, 26, and 28, commencing with first longitudinal end 12 and terminating with second longitudinal end 16. First longitudinal end 12 comprises an adjustable crank and worm gear 29 to adjust the distance of segmented portions 20 and 22 to adapt the table to patients of differing heights. Second longitudinal end 16 contains a similar crank and gear mechanism 30 to adjust segmented portion 28. The adjustment of these segmented portions and the lengthening of same adapts the table for patients of differing heights and also provides the means by which the doctor can provide longitudinal tension to the patient's spine.

Positioned along the longitudinal edge of chiropractic table 10, proximate to segmented portions 24 and 26, are a series of guide tracks 40 and 42 positioned on opposing sides of chiropractic table 10. In this embodiment, guide tracks 40 and 42 comprise two opposing tracks defined by tubular rails 44 and 46 positioned on tracks 40 and 42 parallel to the axis of tracks 40 and 42, but offset 90° from each other. Tubular rails 44 and 46 are designed to slidably accommodate adjustable compressor arms 50. Each guide track 40 can accommodate a plurality of compressor arms 50 and in this embodiment, there are shown two compressor ar3's 50 associated with each guide track 40 and 42. Compressor arms 50 are adjustable along the longitudinal axis of chiropractic table 10 and simultaneously adjustable laterally on chiropractic table 10 along with track guide mechanisms 40 and 42 as will be described hereafter. Each compressor arm 50 contains a locking nut 52 to secure the compressor arm at a longitudinal point in track 40 or 42 to accommodate the patient.

Figure 3:
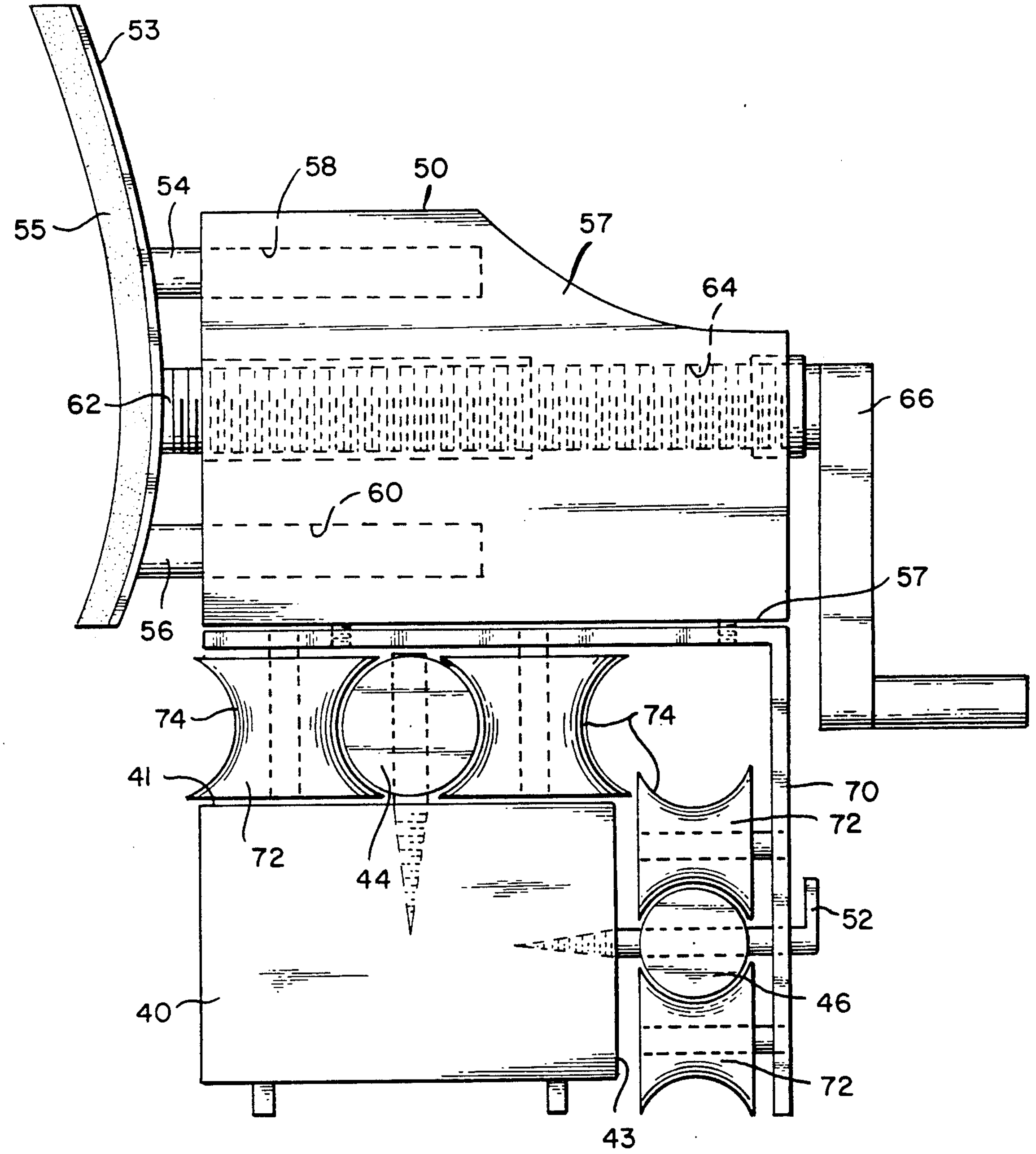
FIG. 3 is an end detailed view of the lateral track mechanism.

Referring to FIG. 3, there is shown an end view of the track guide 40 together with the mounting mechanism for compressor arm 50. Track guide 40 and 42 are identical to each other as are each of the compressor arm mechanisms.

Track 40 is generally rectangular in nature and runs parallel to segmented portions 24 and 26 of chiropractic table 10. As previously discussed, tracks 40 and 42 are removable from the table to allow the patient to position himself on the table at which time either track 40 or 42 could be reinserted to its guide slots. Since chiropractic tables are normally of the width of 20 to 24 inches, guide tracks 40 and 42 are equipped with a gear and crank mechanism 3 to permit tracks 40 and 42 and the compressor arms 50 associated therewith to be moved outwardly to accommodate larger patients.

Referring now specifically to FIG. 3, there is a detailed end view of the compressor arm mechanism mounted to track 40. Track 40 is generally rectangular in shape having longitudinal tubular rails 4 and 46 mounted thereon, tubular rail 44 being mounted to upper surface 41 of track 40 and tubular rail 46 being mounted to the outer side surface 43 of track 40. Tubular rails 44 and 46 are the approximate same length as track 40. The compressor arm mechanism comprises a concave compressor pad 55 mounted to a housing 57. Compressor pad 55 has two guide rails 54 and 56 mounted on outer surface 53 for receipt within channel 58 and 60 of housing 53. This aides in maintaining the alignment of compressor arm 50. Also secured to outer surface 53 of compressor arm 50 is a exterior threaded shaft 62 which passes through housing 57 by means of interior threaded aperture 64. Mounted on one end of threaded shaft 62 is a handcrank 66 which permits the operator to move compressor pad 55 inwardly or outwardly in order to engage the waist, rib cage or hip of the patient.

Compressor arm 50 and housing 57 are mounted on tubular rails 44 and 46 by means of an L-shaped bracket 70 which is mounted to the lower portion 57A of housing 57. L-shaped bracket 70 has a plurality of rollers 72 having circumferential concave sidewalls 74 depending downwardly and inwardly from L-shaped bracket 70. These plurality of rollers 72 engage tubular rails 44 and 46 to provide for the slidable adjustment of compressor arm 50 along guide track 40. In the embodiment shown in FIG. 3, two sets of guide rollers 72, in parallel, would engage tubular rail 44 and two sets of guide rollers 72, in parallel, would engage guide roller 46.

Compressor arm 50 and housing 57 would be slidably secured on tubular rails 44 and 46 by removing guide track 40 from the table and aligning guide rollers 72 such that compressor arm 50 and housing 57 could be slidably inserted on guide rails 44 and 46. The doctor or operator could insert as many compressor arm 50 and housing 57's as desired on each track.

In operation, either track 40 or 42 would be removed from the table to allow the patient to assume the desired position on the table and then track 40 or 42 would be replaced. Compressor arm 50 in combination with tracks 40 and 42 have particular application to a patient whose spinal column deviates laterally from the longitudinal axis of the body. The spinal column would have an arc which, when the patient was reclining on the chiropractic table 10, such arc would bow outwardly towards one lateral side of the table.

In treating such a condition, the physician would align either track 40 or 42 and compressor arms 50 such that compressor arms 50 and pads 55 on the side opposite the curvature, would engage the patient's rib cage, waist or hip at a position proximate to the end of the curvature. The physician would then position one of the compressor arms 50 on the opposite side of the table at the apex of the curvature. The physician then, through the use of handcrank 66 and threaded gear mechanism 62 and 64, can apply measured direct pressure by means of pressure arm 50 and pad 55 at the point of extreme curvature of the spinal column, thus gently and constantly applying pressure to realign the spine.

This alignment aids the physician or chiropractor in realigning the spine, realigning possible slipped disks, or releasing pressure on a pinched nerve.

The slidable alignment of the compressor arms and the amount of pressure transmitted by the compressor arms to the torso of the patient would be determined by the physician or chiropractor based on the particular needs of the patient. However, the design is disclosed herein, permits the physician or chiropractor to apply selective pressure at selective points on the torso of the patient enabling the physician or chiropractor to relieve pain at specific locations.

Two compressor arms are located in order to maintain stability on the upper torso near the chest level and the other pair of compressor pads are located at the hip level. This allows the physician or chiropractor to provide for a three point pressure grip from either the right side or the left side of the patient. The pressure applied by the compressor arms will permit the spine to line up straight and at the same time, while applying slight pressure to the feet, which are being cranked outwardly, the spine is allowed to realign itself. This compression and expansion method is done in a selective manner by the physician and allows the physician to manipulate the spinal column in either direction in a series of gentle moves.

As an additional feature, a cross bar 80 positioned between segmented pads 22 and 24 can be utilized, cross bar 80 having two upright posts 82 for engaging the shoulders or the underarms in order to maintain the shoulders in a correct position while longitudinally or laterally adjusting the spine.

The instant invention has been described in connection with an exemplary embodiment thereof; however it will be understood that many modifications will be apparent to those of ordinary skill in the art and that this application is intended to cover any adaptations or variations thereof. Therefore, it is manifestly intended that this invention be only limited by the claims and equivalents thereof.

I claim:

1. An improved chiropractic table for spinal adjustment of lateral curvature of the spine comprising;

a segmented, padded horizontal table having a first longitudinal end, said first longitudinal end having a headrest for supporting the head of a patient in a prone face-down position, said headrest being generally U-shaped with angularly-shaped sidewalls to conform to the jaw and head configuration of said patient;

a second longitudinal end opposite said first longitudinal end of said segmented padded table, said second end having a plurality of foot stirrups secured thereto and removably attached to said patient's feet, said first longitudinal end and said second longitudinal end being longitudinally adjustable for providing longitudinal tension on said spine;

a plurality of lateral compressor adjustment arms longitudinally, movably disposed on a plurality of longitudinal guide rails disposed between said first longitudinal end and said second longitudinal end of said segmented padded table on the longitudinal sides of said table, said lateral compressor adjustment arms being concave in shape on their interior end to conform to the mid torso shape of said patient, said lateral compressor adjustment arms and said longitudinal guide rails removably secured to said table, said lateral compressor adjustment arms movably disposable inwardly and outwardly, perpendicular to said longitudinal axis of said table, said compressor adjustment arms for contacting and providing pressure to said patient's torso for lateral adjustment of said patient's spine.

2. An improved chiropractic table in accordance with claim 1 wherein said lateral compressor adjustment arms are independently adjustable laterally, inwardly and outwardly, from said patient's torso, said lateral compressor adjustment arms being independently movable longitudinal on said longitudinal guide rails for selectively applying lateral pressure at a predetermined point on either the right or left side of said patient's torso.

3. An improved chiropractic table in accordance with claim 1 wherein said lateral compressor adjustment arms are disposed inwardly or outwardly, perpendicular to the longitudinal axis of said table by means of a gear and handcrank mechanism for selectively applying a predetermined amount of pressure at a predetermined point on said patient's torso.

4. An improved chiropractic table in accordance with claim 1 wherein said lateral adjustment arms are secured in longitudinal position by means of a locking clamp.

5. An improved chiropractic table in accordance with claim 1 wherein said concave shaped end of said lateral compressor adjustment arms are padded with a resilient material for contact with said patient's torso.

6. An improved chiropractic table in accordance with claim 1 wherein positioning posts are positioned proximate to said first longitudinal end of said chiropractic table for engaging the shoulders or underarms of said patient for positioning said patient's shoulders in proper position.

* * * * *